United States Patent
He et al.

(10) Patent No.: US 8,859,587 B2
(45) Date of Patent: *Oct. 14, 2014

(54) (2E)-3-PHENYL-N-[2,2,2-TRIFLUORO-1-[[8-QUINOLINEAMINO)THIOMETHYL] AMINO]ETHYL]-2-ACRYLAMIDE AND PHARMACEUTICAL USES THEREOF

(75) Inventors: Kunlun He, Beijing (CN); Song Li, Beijing (CN); Lili Wang, Beijing (CN); Xin Li, Beijing (CN); Wu Zhong, Beijing (CN); Guoliang Hu, Beijing (CN); Jie Wang, Beijing (CN); Ruijin Li, Beijing (CN); Chunlei Liu, Beijing (CN); Junhai Xiao, Beijing (CN); Long Long, Beijing (CN); Wei Li, Beijing (CN); Hua Chen, Beijing (CN)

(73) Assignee: Chinese PLA General Hospital, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/697,808

(22) PCT Filed: May 14, 2010

(86) PCT No.: PCT/CN2010/000688
§ 371 (c)(1),
(2), (4) Date: Jan. 21, 2013

(87) PCT Pub. No.: WO2011/140682
PCT Pub. Date: Nov. 17, 2011

(65) Prior Publication Data
US 2013/0143917 A1  Jun. 6, 2013

(51) Int. Cl.
*A61K 31/04* (2006.01)
*C07D 215/40* (2006.01)
*A61K 31/47* (2006.01)

(52) U.S. Cl.
CPC ............. *C07D 215/40* (2013.01); *A61K 31/47* (2013.01)
USPC .......................................................... 514/311

(58) Field of Classification Search
CPC ..................................................... A61K 31/47
USPC .................................. 546/159; 514/312, 311
See application file for complete search history.

(56) References Cited

U.S. PATENT DOCUMENTS

2009/0004134 A1 * 1/2009 Obeid ........................ 424/85.1

OTHER PUBLICATIONS

Kerkela, Nature Medicine, VOl 12(8), pp. 908-916, 2006.*
Michael Boyce et al., "A Selective Inhibitor of eIF2 a Dephosphorylation Protects Cells from ER Stress", Science, Feb. 11, 2005, vol. 307, p. 935-939.
International Search Report for Application No. PCT/CN2010/000688 dated Feb. 24, 2011, 3 pages.
Article entitled "Double Identity For Proteins Of The Bcl-2 Family" by John C. Reed, Nature vol. 19 Jun. 1997, 387 773-776.
Article entitled "Protection of Bcl-2 by Salubrinal" by David Kessel, Biochem Biophys Res Commun, Aug. 11, 2006; 346(4): 1320-1323.
EP Search Report, dated Oct. 8, 2013, 4 pages.

* cited by examiner

*Primary Examiner* — D M Seaman
(74) *Attorney, Agent, or Firm* — Howard & Howard Attorneys PLLC

(57) ABSTRACT

The present invention relates to an acrylamide compound of Formula I, or an isomer, pharmaceutically acceptable salt and solvate thereof, to a composition comprising the compound or an isomer, pharmaceutically acceptable salt and solvate thereof, and a pharmaceutically acceptable carrier, excipient or diluent, and to a use of the compound or the composition for prophylaxis and/or treatment of a disease or disorder associated with cardiomyocyte apoptosis.

2 Claims, 1 Drawing Sheet

(2E)-3-PHENYL-N-[2,2,2-TRIFLUORO-1-[[8-QUINOLINEAMINO)THIOMETHYL] AMINO]ETHYL]-2-ACRYLAMIDE AND PHARMACEUTICAL USES THEREOF

RELATED APPLICATIONS

This application is the National Stage of International Patent Application No. PCT/CN2010/000688, filed on May 14, 2010, the content of which is incorporated herein by reference.

FIELD OF THE INVENTION

The present invention relates to the field of medical chemistry, specifically, the present invention relates to a novel acrylamide compound (2E)-3-phenyl-N-[2,2,2-trichloro-1-[[(8-quinolylamino)thiomethyl]amino]ethyl]-2-acrylamide and a pharmaceutical composition thereof, the present invention further relates to the use of the compound and pharmaceutical composition thereof for combating apoptosis, prophylaxis or treatment of a disease or disorder associated with apoptosis, especially for protecting myocardial cells and for prophylaxis or treatment of a disease or disorder associated with apoptosis of myocardial cells.

BACKGROUND OF THE INVENTION

Apoptosis usually refers to programmed cell death of body cells occurred via the regulation of intracellular genes and products thereof during development process or under the action of some factors. Apoptosis commonly exists in biosphere under both physiological state and pathological state. It plays important roles in embryo development and morphogenesis, stability of normal cells in tissues, defense and immune reaction of body, cell damage caused by diseases or poisoning, ageing, generation and development of tumors, and is one of the hottest spots in biomedical research.

Some researches show that the occurrence of many serious diseases relates to the over apoptosis of cells, for example, the reduction of CD4+ T cells during the development of ADIS; the cell death mediated by cytotoxic T cell during transplant rejection reaction; the apoptosis of myocardial cells and nerve cells of ischemia and reperfusion injury; nervous system degradation diseases (such as Alzheimer disease, Parkinson's disease, etc.); apoptosis caused by exposure to ionizing radiation in many tissues.

Some evidences have indicated that cardiomyocytes apoptosis closely associates with the occurrence, development and prognosis of many heart diseases. It is found in the research about cardiomyocytes apoptosis that the infarct of cardiac muscle is not equivalent to myocardial necrosis, and apoptosis is one of mechanisms of myocardial infarction, and is the main manner of myocardial death of early infarction and myocardial death caused by ischemia/reperfusion, and the apoptosis of cardiomyocytes in large amount at this time aggravates myocardial damage. In 1989, Nepomniashchikh et al found in the observation of ultrastructure of hunger myocardial atrophy that the synthesis of cardiomyocytes structural protein decreased, and the cell number decreased but was not accompanied with a proportional decrease of cell nucleus, an thus preliminarily proposed that hunger myocardial atrophy was caused by apoptosis. In 1994, Gottlieb and Kawano et al obtained direct evidences of cardiomyocytes apoptosis by using electron microscope in combination with DNA gel electrophoresis, in which the former disclosed reperfusion injury induced rabbit cardiomyocytes apoptosis, and the latter confirmed that myocarditis patients had concomitant cardiomyocytes apoptosis. Tanaka et al also confirmed the existence of apoptosis of cardiomyocytes in suckling mice. With the progress of methodology and research of apoptosis, pathological functions of cardiomyocytes apoptosis have been found in many heart diseases. Some researches indicate the heart injury in spontaneously hypertensive rat (SHR) is relevant to apoptosis; the conversion from cardiac pachynsis to heart failure in advanced stage is caused by cardiomyocytes apoptosis; acute myocardial infarction also induces apoptosis in early stage of infarction and reperfusion injury, except necrosis; cardiomyocytes apoptosis is also found in transplanted heart and right ventricular maldevelopment myocardial diseases, and anoxia also induces cardiomyocytes apoptosis.

Apoptosis has recoverability in some extents, and the apoptosis in myocardial infarction and ischemia/reperfusion has its own features and regular patterns, so that the features may be used for prevention and reduction of apoptosis and may provide enlightenments for clinical prophylaxis of ischemia/reperfusion injury; during the process of reperfusion, the apoptosis occurred in contraction band region (around infarction site) is induced by some precipitating factors, so that the inhibition factors of apoptosis such as drugs may be used for preventing apoptosis and treating corresponding diseases caused by apoptosis.

However, there are few kinds and numbers of drugs so far that can be clinically used for anti-apoptosis and protecting cells, and their selectivity and targeting property are not satisfied, and therefore it is of great significance to continuously develop new, safe and effective drugs for anti-apoptosis and protecting cells, and especially drugs with a novel mechanism of action.

SUMMARY OF THE INVENTION

The object of the invention is to seek and develop a micromolecule compound for inhibiting apoptosis of myocardial cells for prophylaxis or treatment of various pathological changes caused by apoptosis. The inventors find through long term and massive experimental researches a kind of acrylamide compound that has functions of combating apoptosis and protecting myocardial cells, and can be used for prophylaxis or treatment of diseases or disorders associated with cardiomyocyte apoptosis. Specifically, The first aspect of the present invention relates to a compound of Formula I, or an isomer, pharmaceutically acceptable salt or solvate thereof.

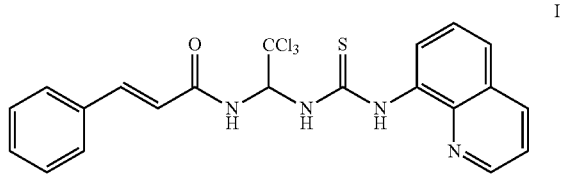

The compound of Formula I has a chemical name of (2E)-3-phenyl-N-[2,2,2-trichloro-1-[[(8-quinolylamino)thiomethyl]amino]ethyl]-2-acrylamide.

Another aspect of the present invention relates to a pharmaceutical composition, comprising a compound of Formula I, or an isomer, pharmaceutically acceptable salt and solvate thereof, a pharmaceutically acceptable carrier, excipient or a diluent.

The present invention further relates to a use of the compound of Formula I or an isomer, pharmaceutically acceptable salt and solvate thereof in manufacture of a medicament for combating apoptosis, preventing or treating a disease or disorder associated with apoptosis.

The present invention further relates to a use of the compound of Formula I or an isomer, pharmaceutically acceptable salt and solvate thereof in manufacture of a medicament for protecting cardiomyocyte and preventing or treating a disease or disorder associated with cardiomyocyte apoptosis.

The present invention further relates to a method for preventing and/or treating a disease or disorder associated with apoptosis, comprising administering a therapeutically effective amount of the pharmaceutical composition.

The present invention further relates to a method for protecting cardiomyocyte, comprising administering a therapeutically effective amount of the pharmaceutical composition.

The disease or disorder associated with cardiomyocyte apoptosis includes but is not limited to: (i) hunger myocardial atrophy, (ii) myocarditis, (iii) heart failure, (iv) myocardial damage caused by primary hypertension, (v) myocardial damage caused by early stage of acute myocardial infarction, (vi) myocardial damage caused by acute myocardial infarction reperfusion, (vii) pathological changes of cardiomyocytes caused by heart transplantation, or (viii) displastic mycocardiosis; or cardiomyocytes apoptosis caused by anoxia, or sclerosis in cardiovascular system.

The compound of the present invention has function of treating chronic heart failure.

By using flow-cytometry test and typical TUNEL apoptosis test, it is found that the pretreatment with the compound of Formula I can significantly improve cardiomyocyte apoptosis induced by tunicamycin, and the protection effect against apoptosis increases with the increase of concentration, which confirms the protection effect of the compound of Formula I for cardiomyocyte apoptosis.

In the present invention, caspase-12 is selected as test object for confirming cell apoptosis path, and the expression of caspase-12 is found in the procedure of cardiomyocyte apoptosis induced by tunicamycin, while the use of the compound of Formula I can reduce the expression of caspase-12, which indicates that the interference of the compound of Formula I can reduce endocytoplasmic reticulum stress and the following expression of caspase-12, thereby alleviating cell apoptosis.

In addition, it is confirmed in the present invention that the compound of Formula I at its maximum cell protection concentration (TD50>100 mM) has no cytotoxic effect, and it does not protect apoptosis stimulation irrelevant to endocytoplasmic reticulum stress.

The present invention further relates to a method for prophylaxis and/or treatment of various diseases caused by cardiomyocyte apoptosis, comprising administering a patient in need thereof a prophylactically or therapeutically effective amount of at least one of the composition of the compound of Formula I or solvate thereof.

Those skilled in the art should appreciate that the compound of the present invention can also be used in form of its pharmaceutically acceptable salt or solvate. The physiologically acceptable salts of the compound of Formula I include conventional salts formed with pharmaceutically acceptable inorganic acid or organic acid or inorganic base or organic base and acid addition salt of quaternary ammonium. More specific examples of suitable acid salts include salts of hydrochloric acid, hydrobromic acid, sulfuric acid, phosphoric acid, nitric acid, perchloric acid, fumaric acid, acetic acid, propionic acid, succinic acid, hydroxyacetic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluene sulfonic acid, methylsulfonic acid, naphthalene-2-sulfonic acid, benzene sulfonic acid, hydroxynaphthoic acid, hydroiodic acid, malic acid, steroic, tannic acid, etc. As for other acids, such as oxalic acid, although they per se are not pharmaceutically acceptable, they can be used for prepare salts as intermediates to obtain the compound of the present invention and pharmaceutically acceptable salts thereof. More specific suitable alkali salts include salts of sodium, lithium, potassium, magnesium, aluminum, calcium, zinc, N,N'-dibenzylethylenediamine, chloroprocaine, choline, diethanolamine, ethylenediamine, N-methylglucosamine, and procaine. The compounds of the present invention as mentioned thereafter include the compound of Formula I and a pharmaceutically acceptable salt and solvate thereof.

The present invention further comprises a prodrug of the compound of the present invention, and once the prodrug is administered, it is chemically converted via metabolic procedure into an active drug. In general, this kind of prodrug is a functional derivative of the compound of the present invention, which can be readily converted into the needed compound of Formula (I). For example, "Design Of Prodrugs", edited by H Bund Saard, Elsevier, 1985, describes conventional methods of selecting and preparing suitable prodrug derivatives.

The present invention also includes any active metabolites of the compound of the present invention.

Another aspect of the present invention relates to a pharmaceutical composition comprising a racemic or optical isomer of the compound of the present invention, and at least one pharmaceutically acceptable carrier, and being useful in in vivo treatment and having biocompatibility. The pharmaceutical composition can be processed into various forms for different administration routes. The compound of the present invention can also be processed into various pharmaceutically acceptable salts.

The pharmaceutical composition of the present invention comprises an effective amount of the compound of Formula I of the present invention or a pharmaceutically acceptable salt or hydrate thereof and one or more suitable pharmaceutically acceptable carriers. The pharmaceutically acceptable carriers comprise but are not limited to: ion exchangers, alumina, aluminum stearate, lecithin, serum protein such as human albumin, buffering substance such as phosphate, glycerol, sorbic acid, potassium sorbate, mixture of partial glycerides of saturated plant fatty acids, water, salts or electrolytes, such as protamine sulfate, disodium hydrogen phosphate, potassium hydrogen phosphate, sodium chloride, zinc salt, colloid silica, magnesium trisilicate, polyvinylpyrrolidone, cellulose substances, polyethylene glycol, sodium carboxymethylcellulose, polyacrylates, beeswax, and lanolin.

The pharmaceutical composition of the compound of the present invention can be administered by any of the following manners: oral administration, spray inhalation, rectal administration, nasal administration, bucca administration, local administration, parenteral administration, such as subcutaneous, intravenous, intramuscular, intraperitoneal, intrathecal, intraventricular, intrasternal, intracranial injection or perfusion, or administration with aid of an explanted reservoir, preferably oral administration, intraperitoneal or intravenous administration.

For oral administration, the compound of the present invention can be processed in any acceptable forms for oral administration, including but not being limited to tablets, capsules, water solutions or water suspensions. The tablets use a carrier generally comprising lactose and maize starch, additionally comprising a lubricant such as magnesium stearate. The capsules use a diluent generally comprising lactose and dry maize starch. The water suspensions usually use a mixture of an active component and suitable emulsifying agent and suspending agent. If necessary, the above oral dosage forms can further comprise some sweetening agents, flavoring agents or coloring agents.

For local administration, especially in treatment of neurogenic disease of a readily accessible affected surface or organ such as eye, skin or inferior part of intestinal tract by local external application, the compound of the present invention can be processed into different dosage forms for local administration according to different affected surfaces or organs, which are illustrated as follows:

For local administration to eyes, the compound of the present invention can be processed in a dosage form of micronized suspension or solution, in which the used carrier is isotonic sterile saline with a certain pH, wherein a preservative such as chlorobenzylalkanol salt can be added or not be added. For the eye use, the compound can be processed into ointment form, such as Vaseline ointment.

For local administration to skin, the compound of the present invention can be processed in suitable dosage forms such as ointments, lotions or creams, wherein the active component is suspended or dissolved in one or more carriers. The carriers usable in ointments include but are not limited to: mineral oil, liquid paraffin, white Vaseline, propylene glycol, polyethylene oxide, polypropylene oxide, emulsified wax and water; the carriers usable in lotions or creams comprise but are not limited to: mineral oil, sorbitan monostearate, Tween 60, hexadecane ester wax, hexadecylene aromatic alcohol, 2-octyldodecanol, benzyl alcohol and water.

The compound of the present invention can further be administered in dosage form of sterile injections, including water or oil suspensions for sterile injection, or sterile injection solutions. The usable carriers and solvents include water, Ringer's solution and isotonic sodium chloride solution. In addition, sterile nonvolatile oil can also be used as solvent or suspending medium, such as monoglyceride or diglyceride.

It should be further pointed out that the dose and usage method of the compound of the present invention depend on many factors, including age, body weight, gender, natural health status, nutritional status, activity of compound, administration time, metabolic rate, severity of disease and subjective judgment of diagnostic doctor.

Beneficial Effects of the Invention

The present invention provides a kind of acrylamide compound, and confirms that it is a potent agent for combating cardiomyocyte apoptosis, and thus its uses include but are not limited to: (i) hunger myocardial atrophy, (ii) myocarditis, (iii) heart failure, (iv) treatment or relief of myocardial damage induced by primary hypertension, (v) treatment or relief of myocardial damage induced at early stage of acute myocardial infarction, (vi) treatment or relief of myocardial damage induced by acute myocardial infarction reperfusion, (vii) treatment or relief of cardiomyocyte pathological change caused by heart transplantation, (viii) treatment or relief of disease of heart muscle caused by maldevelopment; or improvement of sclerosis of cardiovascular system, and thus it provides a new method and approach for treatment of diseases or disorders caused by apoptosis, especially for treatment of diseases or disorders caused by cardiomyocyte apoptosis.

EMBODIMENTS OF THE INVENTION

Figure 1:
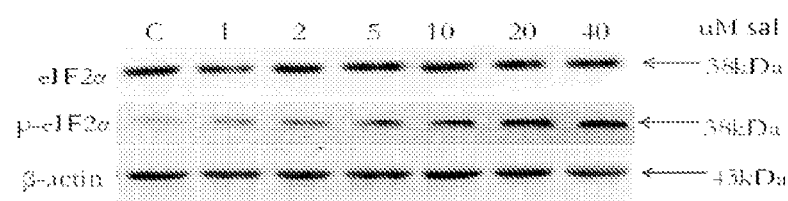
FIG. 1 shows the influences of the compound of Formula I at different concentrations on the expression of elF2α and P-elF2α.

The embodiments of the present invention are illustrated as follows in combination with examples, but those skilled in the art would understand that the following examples are merely to illustrate the present invention and should not be deemed as restriction of the present invention. The examples which specific conditions are not given are performed according to conventional conditions or conditions suggested by manufacturers. The reagents or instruments which manufacturers are not given are all conventional products commercially available from markets.

Example 1

Experimental Research in Protection of Cardiomyocyte Endoplasmic Reticulum Stress-Reduced Apoptosis Animal: newly born Wistar rats, rat age: within 24 h, male and female Separation and Culture of Cardiomyocyte:

The separation and culture of cardiomyocyte refer to the method of differential adhesion separation (Kreider, A. Messing, H. Doan, S. U. Kim, R. P. Lisak and D. E. Pleasure, Enrichment of Schwann cell cultures from neonatal rat sciatic nerve by differential adhesion, *Brain Res* 2 (1981), pp. 433-444.), Wistar neonate rats newly born within 24 h were used to obtain primary cardiac muscle cells.

Effects of the Compound of Formula I at Different Concentrations on Cardiomyocyte Survival Rate as Detected by MTT Method The separated primary culture of cardiac muscle cells as obtained by the above method were inoculated in an amount of $10^4$ cells per well to a 96-well plate, and the volume of each well was 100 µl (marginal wells were filled with sterile PBS). After being cultivated in 5% $CO_2$ and 37° C. incubator for 4 d, they were added with the compound of Formula 1 at different concentrations (0.3 µM, 1 µM, 3 µM, 10 µM, 30 µM, 100 µM), 3 double-wells were set for each concentration, at the same time, zero setting wells (culture medium, MTT, DMSO), and control wells (culture medium, DMSO) were also set. After continuous inoculation for 48 h, each well was added with 20 µl of MTT solution (5 mg/ml, formulated with PBS (pH=7.4), i.e., 0.5% MTT), and the cultivation was continued for 4 h. After the end of cultivation, culture medium in wells was carefully sucked out. Each well was added with 150 µl of DMSO, shaken at a low speed in a shaking table for 10 min, so that the crystal was sufficiently dissolved. The optical density (OD) value of each well was measured at wavelength of 550 nm by enzyme-linked immunoassay instrument, and each well was repeatedly measured for 5 times and the results were recorded. The results are shown in Table 1.

TABLE 1

Effects of the compound of Formula I on cardiac muscle cell survival rate as detected by MTT method

| Experimental Group | Cardiomyocyte survival rate (%) |
|---|---|
| Control group | 100 |
| Drug administration group (0.3 µM) | $98.8562 \pm 6.7316^a$ |
| Drug administration group (1 µM) | $91.6667 \pm 7.6257^a$ |
| Drug administration group (3 µM) | $94.5261 \pm 3.7997^a$ |

TABLE 1-continued

Effects of the compound of Formula I on cardiac muscle cell survival rate as detected by MTT method

| Experimental Group | Cardiomyocyte survival rate (%) |
|---|---|
| Drug administration group (10 μM) | 102.7778 ± 3.0645[a] |
| Drug administration group (30 μM) | 105.8007 ± 3.2639[a] |
| Drug administration group (100 μM) | 104.2484 ± 7.3625[a] |

In comparison with the control group,
[a]$P > 0.05$;

The compound of Formula 1 in a concentration within 100 μM shows no statistic difference of cardiomyocyte survival rate in comparison with the control group, which indicates that the compound of Formula I has no effect on the survival rate of normal cardiac muscle cells.

Effects of the Compound of Formula I at Different Concentrations on Cardiomyocyte Apoptosis Induced by Tunicamycin (TM) as Detected by MTT Method The separated cardiac muscle cells were inoculated in an amount of $10^4$ cells per well to a 96-well plate, and the volume of each well was 100 μl (marginal wells were filled with sterile PBS). After being cultivated in 5% $CO_2$ and 37° C. incubator for 4 d, they were added with the compound of Formula 1 at different concentrations (5 μM, 10 μM, 20 μM) and treated for 30 min, then TM was added to reach a final concentration of 5 μg/ml, at the same time, the TM group with a concentration of 5 μg/ml and the DMSO control group with the same volume were set, 3 double-wells were set for each concentration, at the same time, zero setting wells (culture medium, MTT, DMSO), and control wells (culture medium, DMSO) were also set. After continuous inoculation, each well was added with 20 μl of MTT solution (5 mg/ml, formulated with PBS (pH=7.4), i.e., 0.5% MTT), and the cultivation was continued for 4 h. After the end of cultivation, culture medium in wells was carefully sucked out. Each well was added with 150 μl of DMSO, shaken at a low speed in a shaking table for 10 min, so that the crystal was sufficiently dissolved. The optical density (OD) value of each well was measured at wavelength of 490 nm by enzyme-linked immunoassay instrument, and each well was repeatedly measured for 3 times and the results were recorded. The cell survival rate at each time point was calculated according to: cell survival rate=(A490 of untreated cells of control group−A490 of TM treated cells)/A490 of untreated cells of control group× 100%, and a cell growth curve was drawn by using time as abscissa and optical density as ordinate.

The results are shown in Table 2.

TABLE 2

Effects of the compound of Formula I on the survival rate of TM-induced cardiac muscle cells as detected by MTT method

| Experimental Group | Cell survival rate (%) |
|---|---|
| Control group | 100 |
| TM interference group | 58.8699 ± 10.7785[#] |
| TM + Compound of Formula I group | |
| Compound of Formula I 5 μM group | 82.6106 ± 8.1018* |
| Compound of Formula I 10 μM group | 83.8371 ± 8.2608* |
| Compound of Formula I 20 μM group | 84.6255 ± 5.5519* |
| Compound of Formula I 40 μM group | 85.4139 ± 5.6916* |

In comparison with the DMSO group,
[#]$P < 0.05$; in comparison with the TM group,
*$P < 0.05$;

The results show that the cardiomyocyte survival rate of the TM interference group significantly decreases (p<0.05), and the groups with pretreatment of the compound of Formula I in various concentrations show significant increase of cell survival rate in comparison with the TM group (p<0.05), which indicates that the compound of Formula I can combat the cardiomyocyte apoptosis induced by Tunicamycin (TM), and show protection effect on cardiomyocyte apoptosis induced by TM.

Example 2

Western Blot Detection of Apoptosis Signaling Protein Expression

The cardiac muscle cells obtained by differential adhesion according to the culture method of primary cardiac muscle cells of Example 1 were inoculated to 6-wells plate, $10^6$ cells per well, each well had a volume of 2 ml, cultivated in 37° C., 5% $CO_2$ incubator for 4 d, the compound of Formula I was added to the groups for interference according to the experimental design, continuously cultivated in 37° C., 5% $CO_2$ incubator to the designed time point, SDS spotting buffer solution was added to split cells, 100° C. water bath for 10 min, centrifuged at 4° C. (12000 rpm×10 min), collected supernatant. Nitrocellulose membrane was dipped in a transferring buffer for 15-20 min in advance. Sampled in 50 μg protein/lane, subjected to 10% polyacrylamide gel SDS-PAGE electrophoretic separation, the gel was then tiled in electrotransferring clamp, in which sponge, filter paper, gel, nitrocellulose membrane, filter paper and sponge were mounted from negative electrode to positive electrode in order. Constant current 350 mA, electrotransferred for 45 min. Electrotransferring membrane to PVDF membrane, the nitrocellulose membrane was taken out, the membrane was washed with TBST for 2 min, sealed with 5% defatted milk powder at room temperature for 1 h, added with first antibody (1:1000) and incubated at 4° C. overnight, the membrane was washed with TBST, 3 times×5 min, then HRP-marked second antibody was added, incubated at room temperature for 1 h, washed with TBST, 3 times×5 min, soaked separately with TSM1 and TSM2 for 5 min and 10 min, developed with chromogenic substrates 6.6 μl NBT and 3.3 μl BCIP dissolved in 1 ml of TSM2, after bonds become clear, the reaction was terminated by washing with water. After the end of development, the records were stored by scanning or taking photos.

Test results:

Expression of elF2α and P-elF2α

Western blotting test with action of the compound of Formula I at different concentrations shows, after cardiac muscle cells were cultivated in 5% CO2, 37° C. incubator for 4 d and separately treated with the compound of Formula I at different concentrations (1 μM, 2 μM, 5 μM, 10 μM, 20 μM, 40 μM) for 48 h, the expression levels of elF2α in wells show no significant change, while the expression level of P-elF2α gradually increases with the increase of the concentration of the compound of Formula I (see: FIG. 1).

Expression Change of Caspase-12 and Cleaved Caspase-12

Figure 2:
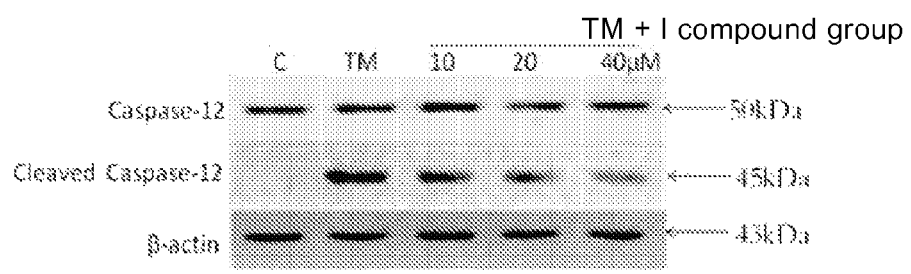
FIG. 2 shows the influences of the compound of Formula I on the expression of caspase-12 and cleaved caspase-12 in cardiac muscle cells induced by TM.

After treatment with the compound of Formula I at different concentrations for 24 h, the groups show no significant change in Caspase-12 expression. Cleaved caspase-12 is not expressed in DMSO group, is obviously expressed in TM (5 μg/ml) induction group, while in the groups with addition of the compound of Formula I at different concentrations (10 μM, 20 μM, 40 μM), the expression of Cleaved caspase-12 gradually decreases with the increase of the concentration of the compound of Formula I. This indicates that Cleaved caspase-12 is activated in the cardiomyocyte apoptosis procedure induced by TM, and the expression level of Cleaved caspase-12 protein decreases in dose dependent manner with the increase of the concentration of the compound of Formula I (see: FIG. 2)

Example 3

Effects of the Compound of Formula I on Cardiomyocyte Apoptosis Induced by TM

The primary cardiac muscle cells obtained by the method according to the culture method of primary cardiac muscle cells of Example 1 were added with tunicamycin (TM) on the 4$^{th}$ day to perform interference test. The cells were randomly divided into 5 groups: solvent control group (DMSO), TM interference group (5 μg/ml), Compound of Formula I+TM interference group (10 μM+5 μg/ml), Compound of Formula I interference group (20 μg/ml+5 μg/ml), Compound of Formula I interference group (40 μg/ml+5 μg/ml).

Apoptosis Detection by Flow Cytometer:

it is 24 h after drug interference, the cells were treated by the method of AnnexinV-FITC apoptosis kit, and the apoptosis was detected within 1 h by using a flow cytometer (BD ACScalibur, US Becton-Dickinson Company). For each sample, 14000 cells were collected and analyzed, the test was repeated for 3 times, and the average value was used as a result.

TUNEL Detection:

It was 24 h after drug interference, the apoptotic cells were detected by terminal deoxynucleotidyl transferase-mediated biotinylated UTP nick end labeling (TUNEL) method, and the cells were treated according to the specification of kit. The cells treated with 0.1 mg/ml DNase I and growing on a glass slide were used as positive control. 5 or more visual fields were randomly selected under light microscope, the apoptotic cells (brown yellow granules seen in nucleus) among the cells were counted. Apoptosis rat=(number of positively stained nuclei/number of all nuclei)×100%.

Test Results:

Comparison of apoptosis rates of the groups

Detected by Flow Cytometer, the normally cultured neonate rats had a cardiomyocyte early apoptosis rate of 12.72%; after being induced with 5 μg/ml TM for 24 h, the apoptosis rate reached 29.98%; in comparison with the TM group, the 10 μM Compound of Formula I group, 20 μM Compound of Formula I group, and 40 μM Compound of Formula I group had significantly decreased apoptosis rates (P<0.05), and the apoptosis rates showed a decline trend with the increase of dose. See Table 3.

TABLE 3

Effects of the compound of Formula I on cardiomyocyte apoptosis induced by TM

| Group | Cardiomyocyte apoptosis rate detected by flow cytometer (%) |
| --- | --- |
| Control group (DMSO) | 12.72 ± 0.96 |
| TM interference group | 29.98 ± 1.22[a] |
| TM + Formula I 10 μM | 22.98 ± 1.35[ab] |
| TM + Formula I 20 μM | 20.13 ± 0.87[ab] |
| TM + Formula I 40 μM | 18.64 ± 0.83[ab] |

In comparison with the DMSO group,
[a]P < 0.05; in comparison with the TM group,
[b]P < 0.05

TUNEL Detection Results

The apoptosis rate of the DMSO group was 7.86%, after being induced with 5 μg/mL TM for 24 h, the apoptosis rates of the interference groups increased significantly (P<0.05), in comparison with the TM interference group, the groups with the addition of Compound of Formula I (10 μM, 20 μM, 40 μM) had a significant decrease in apoptosis rate (P<0.05). The Compound of Formula I 40 μM group had a significant decrease in apoptosis rate in comparison with the Compound of Formula I 10 μM, 20 μM groups (P<0.05)

TABLE 4

Comparison of cardiomyocyte apoptosis rates ($\bar{x} \pm s$, n = 6)

| Group | TUNEL detection (%) |
| --- | --- |
| Solvent (DMSO) control group | 7.86 ± 0.94 |
| TM interference group | 30.84 ± 1.26[a] |
| TM + Formula I 10 μM group | 25.75 ± 0.97[b] |
| TM + Formula I 20 μM group | 24.94 ± 0.82[b] |
| TM + Formula I 40 μM group | 21.15 ± 0.85[b c] |

In comparison with the DMSO group,
[a]P < 0.05; in comparison with the TM group,
[b]P < 0.05; in comparison with the TM + Formula I 10 μM group and the TM + Formula I 20 μM group,
[c]P < 0.05

Example 4

Protection Effects of the Compound of Formula I on Cardiomyocyte Apoptosis Induced by Anoxia Animals:

neonate Wistar rats, rat age: within 24 h, male and female

Preparation of Cells:

cardiac muscle cells were separated and cultured by referring to the method of differential adhesion, Wistar neonate mice newborn within 24 h were used, sterilized at skin of ventrum with iodine tincture and ethanol, subjected to thoracotomy using scissors at subxiphoid median line with a deviation to left, heart was taken out after slant thoracotomy and placed in PBS precooled with ice; the heart was softly blown and beaten with 0.01M PBS to remove blood cells and other tissues, then cut into pieces with 0.5 mm$^3$ size, washed with 0.01M PBS repeatedly for 2-3 times; the pieces were placed in conical flask, added with 4 ml of 0.125% pancretin, 1 ml of 0.1% collagenase II (final concentrations separately being 0.1% and 0.02%), shaken in 37° C. water bath for 10 min, the supernatant was discarded; then 4 ml of 0.125% pancretin and 1 ml of 0.1% collagenase II again, shaken in 37° C. water bath for digestion for 10 min, the supernatant was sucked and transferred to a centrifuge tube, and the supernatant was added with DMEM containing 10% FBS to terminate digestion; the step of shaking and digestion in water bath was repeated for 3-4 times, until the tissue pieces were completely digested; the collected cell suspension was centrifuged under 1000 rpm for 10 min, the supernatant was removed, then a culture medium was added for resuspension; the resuspended cells were inoculated in a cell culture flask, placed in CO2 incubator at 37° C. for incubation for 1.5 h, then the culture medium was sucked out, countered under microscope, then DMEM culture medium containing 10% FBS was used to adjust cell density, inoculated in an amount of 1×10$^4$ to a 96-well plate, placed in 5% CO2 incubator at 37° C. for 24 h, then half medium was replaced, a culture medium containing 0.1% Brdu was supplementally added; then the medium was replaced once per 48 h, and primary cardiac muscle cells were obtained after 4 days of cultivation.

Preparation of Solutions (the following reagents were purchased from Invitrogen Company):

1) 1× Wash Buffer: 20 mL of 10× Wash Buffer was added to 180 mL of ultrapure water, stored at 4° C. for 7 days.

2) fixing solution: 7.3 mL of 37% formaldehyde solution was added to 14.7 mL of 1× Wash Buffer, pre-heated before use to 37° C. j 3) 1× penetrating buffer solution: 4 mL of 10× penetrating buffer solution was added to 36 mL of double distilled water, this application solution was stored at 4° C. for 7 days.

4) Mitotracker/Hoechst solution (stored at −20° C.): Mitotracker was dissolved with 94 µl of anhydrous DMSO to obtain 1 mM solution, this solution could be preserved at −20° C. under dry and dark condition for 6 months. In order to avoid multiple freeze-thaw cycles, it was subpackaged in an amount for single use. 5.5 µl of 1 mM Mitotracker Solution and 11 µl of Hoechst dye solution were added to cell culture medium, to obtain an application solution with a final volume of 5.5 mL. This application solution should be prepared when using.

5) Alexa Fluor 488 Phalloidin solution: Alexa Fluor 488 Phalloidin was dissolved with 140 µL of methanol to form a mother liquor, this solution could be preserved at −20° C. under dry and dark condition for 12 months. 27.5 µL of the Alexa Fluor 488 Phalloidin mother liquor was added to 5.5 mL of 1× Wash Buffer to prepare an application solution. This application solution should be prepared when using.

Experimental Steps:

1. The separated cardiac muscle cells were inoculated to a 96-wells plate, $10^4$ cells per well, and the volume of each well was 100 µl (marginal wells were filled with sterile PBS). After being cultivated in 5% CO2 and 37° C. incubator for 4 d, Formula I was separated added at different concentrations (5 µM, 10 µM, 20 µM) and treated for 30 min, then placed in a sealed 37° C. anoxia incubator (O2/CO2, 5:95) and continuously incubated for 16 h, and at the same time, anoxia control wells and the normal control wells were set and cultivated in 5% CO2, 37° C. incubator for 16 h.

2. It was 30 min before the anoxia incubation was finished, each well was supplemented with 50 µl of culture medium and 50 µl of Mitotracker/Hoechst solution, and the cells were continuously incubated at 37° C. for 30 min.

3. 100 µl of the fixing solution was preheated to 37° C. and separately added to each culture well, without sucking out culture medium, and incubation was performed under ventilation at room temperature for 10 min.

4. The solution of each well was sucked out (the plate could be struck), washed with 1× Wash Buffer (100 uL/well) once. Carefulness was kept during operation and washing procedure, and slow sucking and adding liquid to maintain cell adhesion and integrity.

5. Wash Buffer was sucked out, 1× penetrating buffer solution (100 uL/well) was added, incubated at room temperature for 15 min.

6. The penetrating buffer solution in each well was sucked out, washed once with 100 µL/well of 1× Wash Buffer.

7. The Wash Buffer in each well was sucked out (the plate could be struck), each well was added with 50 µl of Alexa Fluor 488 Phalloidin Solution, incubated at room temperature in dark for 30 min.

8. The Alexa Fluor 488 Phalloidin solution in each well was sucked out, washed with 1× Wash Buffer (100 µl/well) twice, and added with 1× Wash Buffer (100 µl/well).

9. The edge of plate was covered with a sealing membrane (for prevention of drying), and assayed with HCS Reader.

High Connotation Screening Analytical Method:

When apoptosis occurs, there usually are significant change in cytomorphology and a series of changes in biochemistry and molecular markers. Many methods are developed for detecting apoptosis, but most of them detect single index of apoptosis. High connotation screening analytical method is a method for detecting apoptosis newly developed in recent years, which uses specific fluorescence staining to analyze apoptosis with a plurality of factors. Three parameters relevant to apoptosis process were mainly analyzed, including karyomorphology change, mitochondrial swelling and/or mitochondrial transmembrane potential, F-actin content. It has high specificity and reliability for integral cells.

Apoptotic cells usually exhibit two types of nucleic changes, nuclear fragmentation or nuclear concentration. During the procedure of nuclear fragmentation, spherical or elliptic nucleus becomes lobulated shape, and finally split into a plurality of subuncleus structures. The density of nucleus increases due to the destruction of structural ingredients such as autosomes and nucleoli in nuclei. HCS Reader can observe morphology of nucleus by Hoechst staining, and can compare quantitatively nucleus area and nucleus strength.

Intramitochondrial changes are important morphologic changes for apoptosis. Mitochondrion releases apoptotic genetic factors through outer membrane, at the same time, the increase of mitochondrial permeability may also cause changes of electrochemical ingredients of mitochondrial inner membrane, resulting in the decrease or disappear of membrane potential. Under the stimulation of apoptosis, mitochondrion is also extended and enlarged, causing the increase of mitochondrial volume. The decrease of mitochondrial membrane potential and the increase of mitochondrial volume are generally accepted as markers of early apoptosis, and can be quantitated by mitochondrial tracer MitoTracker® Red.

The change of actin cytoskeleton has been reported as an important parameter relevant to apoptosis change, and F-actin content increases during the early stage of apoptosis. F-actin content can be determined by staining with a F-actin specific staining agent Alexa Fluor® 488 Phalloidin, so as to perform quantitative comparison of apoptosis extent.

The detection results of the protection effects of Compound of Formula I on cardiomyocyte apoptosis induced by anoxia are as follows:

1) Test results of nucleus area:

| Group | Nucleus area |
| --- | --- |
| Control group | 113.86 ± 3.06 |
| Anoxia group | 98.26 ± 1.00 |
| Compound of Formula I 5 µM group | 109.90 ± 3.97 |
| Compound of Formula I 10 µM group | 107.43 ± 7.77 |
| Compound of Formula I 20 µM group | 111.90 ± 10.76 |

2) Test results of nucleus strength:

| Group | Nucleus strength |
| --- | --- |
| Control group | 122.70 ± 2.38 |
| Anoxia group | 118.23 ± 1.33 |
| Compound of Formula I 5 µM group | 124.90 ± 2.25 |
| Compound of Formula I 10 µM group | 123.21 ± 2.71 |
| Compound of Formula I 20 µM group | 121.40 ± 2.24 |

3) Test results of light flux:

| Group | light flux |
| --- | --- |
| Control group | 1247.52 ± 48.059 |
| Anoxia group | 1044.91 ± 16.53 |
| Compound of Formula I 5 μM group | 1201.92 ± 29.95 |
| Compound of Formula I 10 μM group | 1166.12 ± 91.06 |
| Compound of Formula I 20 μM group | 1214.09 ± 107.59 |

4) Test results of actin filament:

| Group | Filament strength | Short/long axis ratio of filament |
| --- | --- | --- |
| Control group | 461.77 ± 8.68 | 0.74 ± 0.00 |
| Anoxia group | 541.01 ± 41.14 | 0.77 ± 0.01 |
| Compound of Formula I 5 μM group | 498.03 ± 76.67 | 0.75 ± 0.02 |
| Compound of Formula I 10 μM group | 503.64 ± 49.23 | 0.74 ± 0.01 |
| Compound of Formula I 20 μM group | 471.83 ± 69.38 | 0.74 ± 0.02 |

5) Test results of mitochondrial transmembrane potential:

| Group | Transmembrane potential |
| --- | --- |
| Control group | 1 ± 0.01 |
| Anoxia group | 96.04% ± 3.61% |
| Compound of Formula I 5 μM group | 96.69% ± 5.06% |
| Compound of Formula I 10 μM group | 97.19% ± 2.82 |
| Compound of Formula I 20 μM group | 99.40% ± 2.80% |

6) Test results cell count:

| Group | Cell count |
| --- | --- |
| Control group | 1 ± 0.11 |
| Anoxia group | 71.51% ± 5.73% |
| Compound of Formula I 5 μM group | 88.57% ± 7.64% |
| Compound of Formula I 10 μM group | 98.03% ± 16.24 |
| Compound of Formula I 20 μM group | 101.73% ± 22.42% |

In comparison with the control group, the anoxia group has a cell count decreased by 28.49%, while after using Compound of Formula I at different concentrations (5 μM, 10 μM, 20 μM), the cell counts increase (by 17.06%, 26.52% and 30.22%) in comparison with the anoxia group.

In comparison with the control group, the anoxia group shows decreases in nucleus area, nucleus strength, light flux, actin filament, mitochondrial transmembrane potential and cell count, while Compound of Formula I can significantly improve the above indexes of cardiac muscle cells under highly anoxia condition. The high connotation screening results indicate that the compound of Formula I has significant effects in improving cardiomyocyte apoptosis induced by anoxia.

Although the specific modes for carrying out the invention have been described in details, those skilled in the art would understand that according to the disclosed teachings, these details could be subjected to various modifications and replacements, and all of these alternations are covered by the protection scope of the present invention. The protection scope of the present invention is determined by the attached claims and any equivalents thereof.

What is claimed is:

1. A method for treating a disease or disorder associated with cardiomyocyte apoptosis induced by Tunicamycin or anoxia, comprising administering a therapeutically effective amount of a compound of Formula I or a pharmaceutical composition comprising said compound,

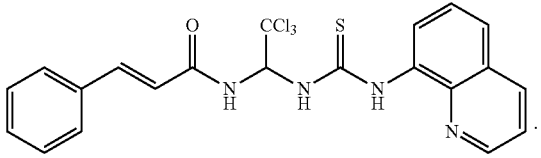

Formula I

2. The method according to claim 1, wherein the disease or disorder associated with the cardiomyocyte apoptosis is induced by anoxia.

* * * * *